United States Patent [19]

Jackson

[11] Patent Number: 5,593,851

[45] Date of Patent: *Jan. 14, 1997

[54] TEST KID FOR THE RAPID DETECTION OF HELICOBACTER PYLORI IN GASTRIC BIOPSY TISSUE

[75] Inventor: Frank W. Jackson, Camp Hill, Pa.

[73] Assignee: Chek-Med Systems, Inc., Camp Hill, Pa.

[*] Notice: The term of this patent shall not extend beyond the expiration date of Pat. No. 5,439,801.

[21] Appl. No.: 392,670

[22] Filed: Feb. 23, 1995

Related U.S. Application Data

[63] Continuation of Ser. No. 221,311, Apr. 1, 1994, abandoned.

[51] Int. Cl.$^6$ .............................. C12Q 1/58; C12Q 1/62; C12Q 1/04
[52] U.S. Cl. ................. 435/12; 435/10; 435/34; 435/810
[58] Field of Search .................. 435/12, 10, 34, 435/294, 810; 128/749, 757; 206/210, 473–475; 436/165, 808, 809, 811

[56] References Cited

U.S. PATENT DOCUMENTS

| | | | |
|---|---|---|---|
| 3,145,086 | 8/1964 | Free et al. | 23/253 |
| 3,249,513 | 5/1966 | Babson | 195/66 |
| 3,395,082 | 7/1968 | Mast | 195/103.5 |
| 4,748,113 | 3/1988 | Marshall | 435/12 |
| 4,803,983 | 2/1989 | Siegel | 128/321 |
| 5,182,191 | 1/1993 | Fan | 435/7.9 |
| 5,314,804 | 5/1994 | Boguslaski | 435/12 |
| 5,439,801 | 8/1995 | Jackson | 435/12 |

FOREIGN PATENT DOCUMENTS 1112251  5/1968  United Kingdom .

OTHER PUBLICATIONS

Cellini, L., New Plate Medium for Growth . . . J of Clin Micro May 1992, vol. 30 #5 pp. 1351–1253.

Pyloric Campylobacter Infection and Gastroduodenal Disease. Med J Aust 1985; 149:439–444, Marshall et al.

Helicobacter pylori: Its Epidemiology and Its Role in Duodenal Ulcer Disease, J. Gastroenterol Hepatol 1991; 6:105–13, D. Y. Graham.

Helicobacter pylori Infection and the Risk of Gastric Cancer; N. Engl. J. Med 1991; 325:1127, Parsonnet et al.

Effect of Rantidine and Amoxicillin Plus Metroidazole on the Eradication of Helicobacter pylori and the Recurrence of Duodenal Ulcer. N Engl J. Med 1993; 328: 308–12, Hentschel et al.

Can One Use the Results of Seriologic Testing to Monitor the Results of Therapy of Helicobacter pylori? Gastroenterology 1991; 100:A62. Evans et al.

Remel Catalog No. 102, T. I. No. 20389 Date Unknown.

Primary Examiner—Ralph Gitomer
Attorney, Agent, or Firm—Eugene Chovanes

[57] ABSTRACT

A test kit for the rapid detection of the bacteria *Helicobacter pylori* in gastric biopsy tissue to diagnose gastric disease is described which includes a chemical test composition for the bacteria, a tray-like means including means to visibly display the test composition, means to handle a biopsy specimen and insert it in the test composition, and indicia to determine the results of the test.

3 Claims, 2 Drawing Sheets

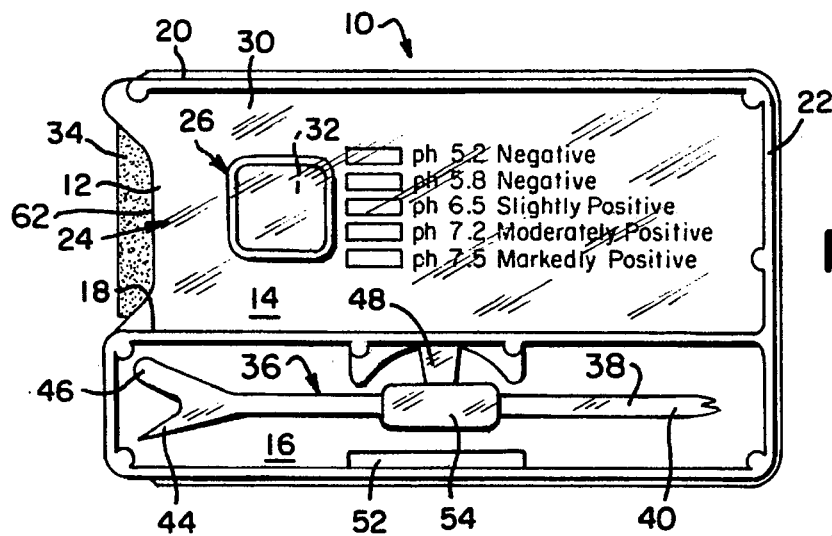
FIG. 1
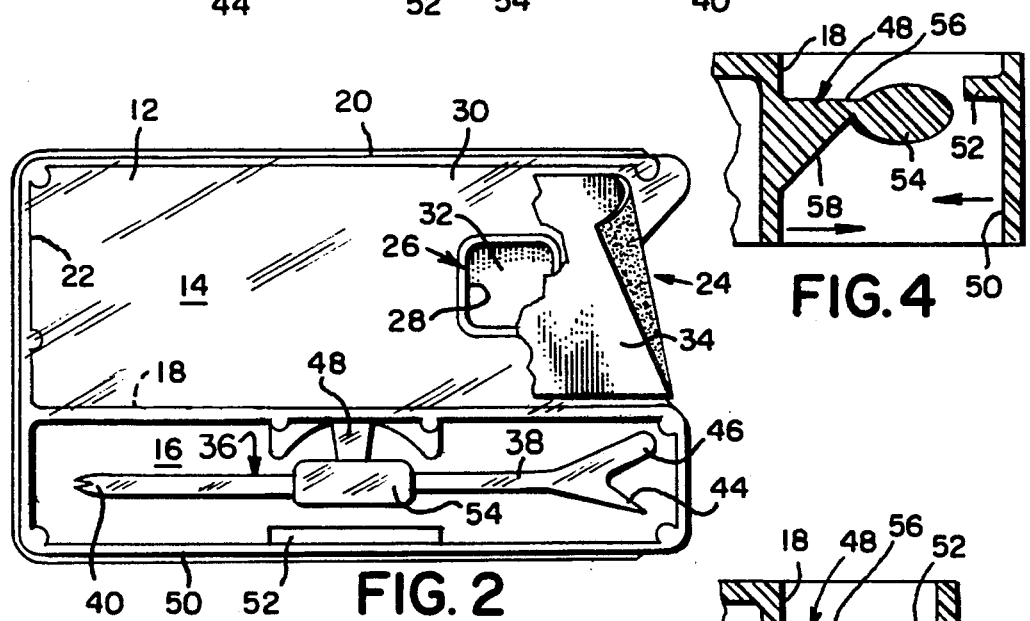
FIG. 2
FIG. 4
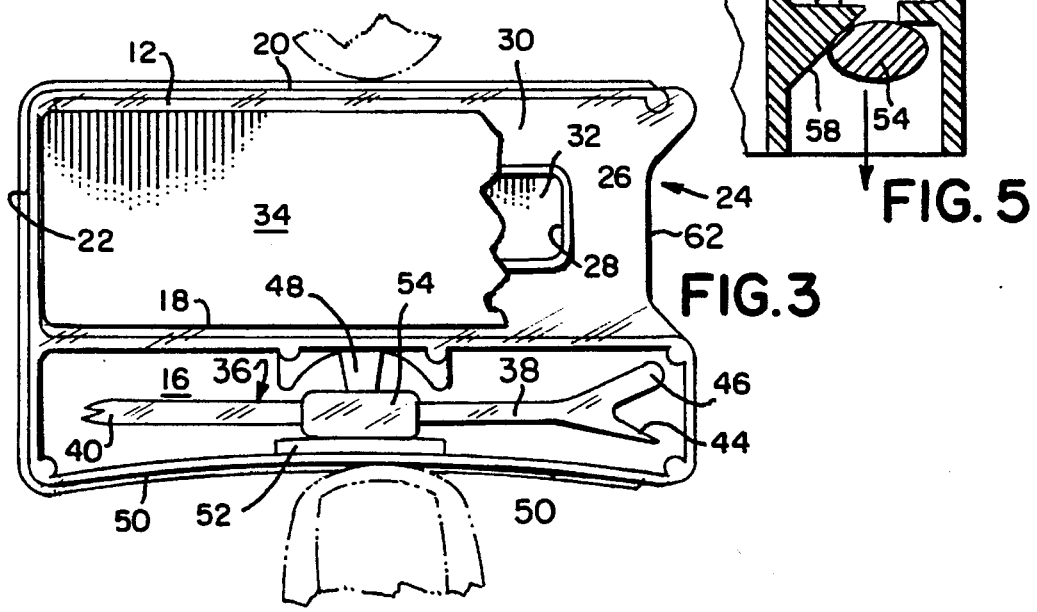
FIG. 3
FIG. 5

TEST KIT FOR THE RAPID DETECTION OF HELICOBACTER PYLORI IN GASTRIC BIOPSY TISSUE

This application is a continuation of application Ser. No. 08/221,311, filed Apr. 1, 1994, now abandoned.

The present invention relates to a test kit for use in the rapid diagnosis of gastric disease by the detection of *Helicobacter pylori* bacteria in a gastric biopsy specimen. The test kit includes means for handling a biopsy specimen and a test composition containing urea and a combination of dye indicators as described in my U.S. Pat. No. 5,439,801 granted Aug. 8, 1995; the entire disclosure of said application being incorporated herein by reference.

It has become well-established that (1) the bacteria *Helicobacter pylori* causes chronic active gastritis (see the annexed Bibliography for the numbered references), and that (2) virtually all patients suffering from duodenal ulcer and perhaps 80% of patients having gastric ulcers are infected by *H. pylori*. There is also epidemiological evidence that (3) correlates the presence of *H. pylori* with gastric cancer. In view of these facts, a test for the presence of *H. pylori* in a gastric biopsy specimen has become the preferred method for the diagnosis of gastric disease.

The purpose of the present invention is to provide an improved test kit for the rapid, convenient, reliable and accurate detection of *H. pylori* in gastric biopsy tissue.

BACKGROUND AND PRIOR ART

An extensive description of the background and prior art for the diagnosis of gastric disease by the detection of *H. pylori* in gastric tissue is set forth in my U.S. Pat. No. 5,439,801 granted Aug. 8, 1995 and is incorporated herein above by reference.

Briefly, it having been seen that the bacteria *H. pylori* is present in endoscopically obtained gastric biopsy specimens from both gastric and duodenal ulcer patients and it being known that the enzyme urease is always associated with that bacteria, the concept of diagnosing the presence of such ulcers by testing biopsy specimens for urease suggested itself. Chemical tests for urease were already known in the art. In one such test a urea-containing broth provides a positive urease reaction (hydrolysis of urea) as below:

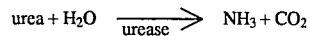

$$\text{urea} + H_2O \xrightarrow{\text{urease}} NH_3 + CO_2$$

as indicated by a change in color of the indicator Bacto phenol red from yellow (pH 6.8) to red to cerise at pH 8.1 or more alkaline due to the production of ammonia and/or ammonium carbonate by the urea-urease reaction. See the Difco Manual, 9th edition, Difco Laboratories, Detroit, Mich., (1953). The urea broth described in the Difco Manual was apparently used by B. J. Marshall in the work described in the Rapid Diagnosis of Campylobacteria associated with Gastritis, The Lancet, Jun. 22, 1985.

This type of urease test has come into commercial clinical use. In the United States a commercial test product is marketed under the trademark "CLOtest®". This product is described in U.S. Pat. No. 4,748,113 issued to Barry J. Marshall on May 31, 1988. The test of the Marshall patent commercially employs urea, a buffer, a bactericide, and phenol red as the dye indicator. This test is carried out in an alkaline pH range showing a positive result on a change of the indicator from yellow to red at a pH in the range from about 6.8 to 9.

In the Marshall test, a gastric mucosal biopsy specimen containing *H. pylori* is placed in solution or an aqueous agar gel containing urea, and indictor, phenol red, and buffers. The urease in *H. pylori* converts urea to ammonia which raises the pH and turns the agar color from a yellow to red, indicating a positive test. According to the package insert in the Marshall commercial phenol red test (CLOtest®)it is recommended that the test be incubated at 30°–40° C. for three hours and it is indicated that it may take up to 24 hours to develop a positive test. This test relies on the passive diffusion of urease from the cell wall of the bacterium into the agar gel testing solution. Moreover, operating as it does at a pH above 6.5, the test may give a positive result with bacteria other than *H. pylori* and thus is not entirely specific for *Helicobacter pylori*. Specifically, Proteus, Pseudomonas, and *E. Coli*. species may cause a color change at this level and give a false positive test.

Another test kit for *H. pylori* is available commercially from Serim Research Corporation, 1000 Randolph St., Bldg. 17, c/o Miles Inc., Elkhart, Ind. 56515 under the trademark "PyloriTek". This kit includes test strips having a substrate pad containing 3.3% urea and, in a separate matrix, a reaction pad containing 0.1% bromophenol blue dye indicator and 0.2% sulfamic acid. The test kit also contains, in a separate container, a hydration solution consisting of 1.8% Tris buffer. This kit makes use of the same urease-urea reaction as the Marshall test to produce gaseous ammonia which changes the bromophenol blue from its original yellow color to make a blue test spot over a biopsy specimen on a yellow field to indicate a positive test. This test is said to be readable in 120 minutes and should not be read after that time to avoid false positives. While the two-hour usual test time is an improvement, it is apparent that an even more rapid and less complicated test would be desirable.

SUMMARY OF THE INVENTION

The present invention resides in the provision of a compact test kit for detecting *H. pylori* in a gastric biopsy specimen which comprises a closed well or reaction vessel containing a gelled test composition, means for exposing the well, and means for introducing the biopsy specimen to the gelled test composition in the well. The kit may also be provided with means to record pertinent data as to the patient's identity and the time and date of the test. The kit may also include means to seal the well after use. The kit may also be provided with a color spectrum for determining the results of the test by comparison with the color change of a combination of dye indicators in the test composition. The test composition is disclosed in detail in my U.S. Pat. No. 5,439,801 issued Aug. 8, 1995 referred to above.

BRIEF DESCRIPTION OF THE DRAWINGS

The invention will now be described in greater detail in conjunction with the accompanying drawings, in which:

FIG. 1 is a top plan view of a preferred test kit;

FIG. 2 is a bottom plan view of the test kit of FIG. 1;

FIG. 3 is another bottom plan view of the test kit of FIGS. 1 and 2, showing a peelable label partially stripped away to uncover a gel-containing well in the test kit, and also showing the operation of means for removal of a biopsy pick from the test kit;

FIGS. 4 and 5 are detail drawings on an enlarged scale showing the means for removal of the biopsy pick from the test kit of FIGS. 1, 2 and 3;

DETAILED DESCRIPTION OF THE INVENTION

Figure 6:
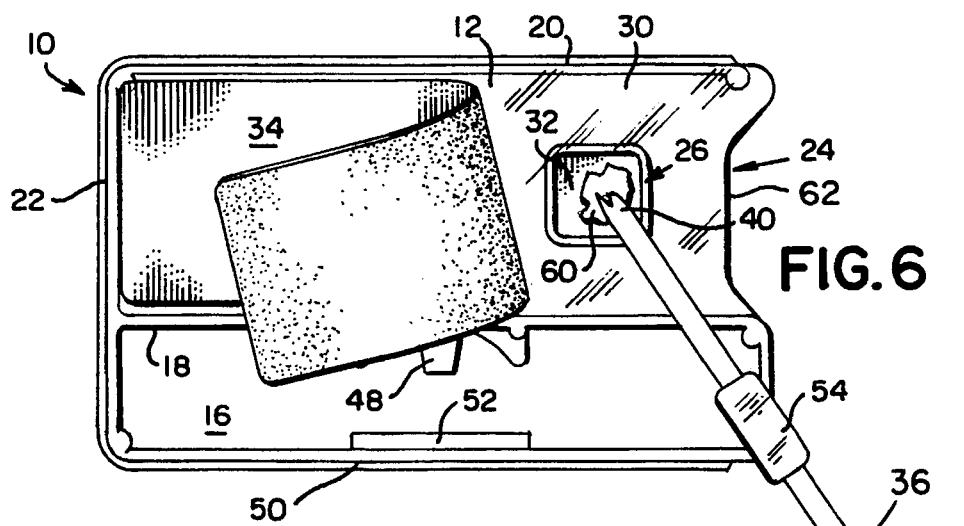
FIG. 6 is a bottom plan view of the test kit of FIGS. 1–5 showing the use of the biopsy pick in placing a biopsy specimen in the gel in the test well.

Referring now to the accompanying drawings, a preferred test kit of the invention 10 has a body member 12 including an upwardly open tray divided into two compartments 14 and 16 by a longitudinally extending upright partition wall 18. Two outer edges of the larger open compartment 14 are closed by upstanding walls 20 and 22. Upstanding partition 18 closes a third inner side of compartment 14, the fourth side of compartment 14 being open at 24. The larger compartment 14 of the tray in the test kit contains a well 26 integral with the base 30 of the compartment 14. The well 26 is open at 28 through base 30 of compartment 14 but is closed on its four sides and the bottom 32 which is upward in FIG. 1 and downward in FIG. 2. The well 26 is preferably transparent although it is only necessary that it be open at 28 to make its contents visible.

The well 26 is filled with a test composition 32 containing urea and a dye indictor which changes color when a gastric biopsy specimen containing *Helicobacter pylori* is placed in the well. The well 26 containing the test composition 32 is closed at its open side 28 by a peelable sealing means 34 which extends over an indentation 62 in the open end 24 of compartment 14. The peelable sealing means 34 is peelably adhered to the back of lower surface 30 of the compartment 14.

A means for handling a biopsy specimen is removably mounted in the second longitudinal compartment 16 which is upwardly and downwardly open as shown in FIGS. 1, 2 and 3. The means for handling the biopsy specimen is preferably a pick 36 having an elongated shaft 38 having a tapered bifurcated point 40 at one end and a forked 42 device at the other end including a sharp point 44 and a blunt prong or spatula 46.

The means for handling a biopsy specimen such as the pick 36 is removably mounted in the compartment 16 by any suitable means such as by an adhesive or by a frangible integral molded joint. In the preferred embodiment shown in FIGS. 1, 2 and 3, the pick 36 is integrally but frangibly molded with a boss 48 which is firmly molded with or mounted on the wall 18 and extending into the compartment 16. The longitudinal compartment 16 containing the pick 36 has a deformable outer wall 50 which may optionally have a boss 52 extending into compartment 16 adjacent to or in contact with the pick 36. The pick 36 preferably has an enlargement 54 at the center of its shaft 38 intermediate the boss 48 and boss 52. The pick 36 is broken away from its frangible connection with boss 48 by deformation of the wall 50, by thumb pressure of the user or otherwise, to press the wall 50 inwardly to force the boss 52 into contact with the enlarged portion 54 of the pick to break it away from its frangible mounting on the boss 48.

An especially preferred embodiment of the means for mounting and demounting the pick is shown in FIGS. 4 and 5 in which the preferred configuration of the boss 48 extends outwardly from the inner wall 18 of the compartment 16 and has an upper planar side 56 and a lower slanting side 58 and a generally triangular cross section. The central enlarged portion 54 of the pick is frangibly connected to the under side of the lower slanting edge 58 of the flange 48. As the wall 50 is deformed inwardly by thumb pressure as shown in FIG. 3, the enlarged portion 54 of the pick is forced against the slanted surface 58 of the boss 48 until the connection is broken between the pick and flange and the pick is freed from its mounting.

Figure 7:
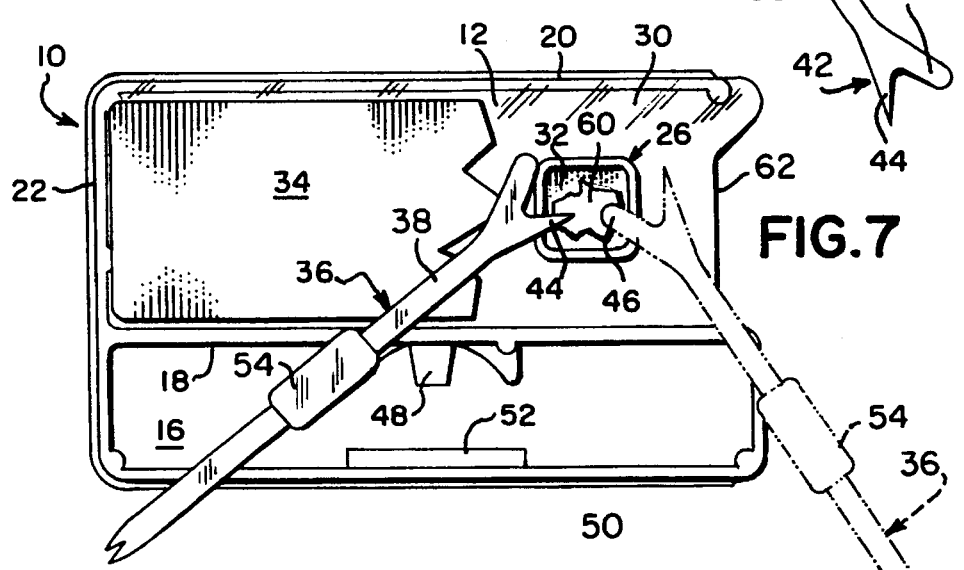
FIG. 7 shows the use of the forked end of the biopsy pick in manipulating the biopsy specimen in the test well.

Having freed the pick 36, it may be used as shown in FIGS. 7 and 6 to pick up the biopsy specimen by the point 44 as in FIG. 7 and to force it into the test composition 32 in the well 26 with the bifurcated point 40 as seen in FIG. 6. As shown in FIG. 7, the spatula 46 of forked end 42 of the pick 36 may alternatively be used to place the biopsy specimen in the test composition, as seen in phantom. In other words, the specimen is placed in the well 26 with either spatula 46 or point 44 of the pick 36, and then submerged in composition 32 with bifurcated point 40. Point 40 does not pierce the specimen so there is no tendency to pull the specimen out of the composition upon withdrawal of the pick.

Figure 8:
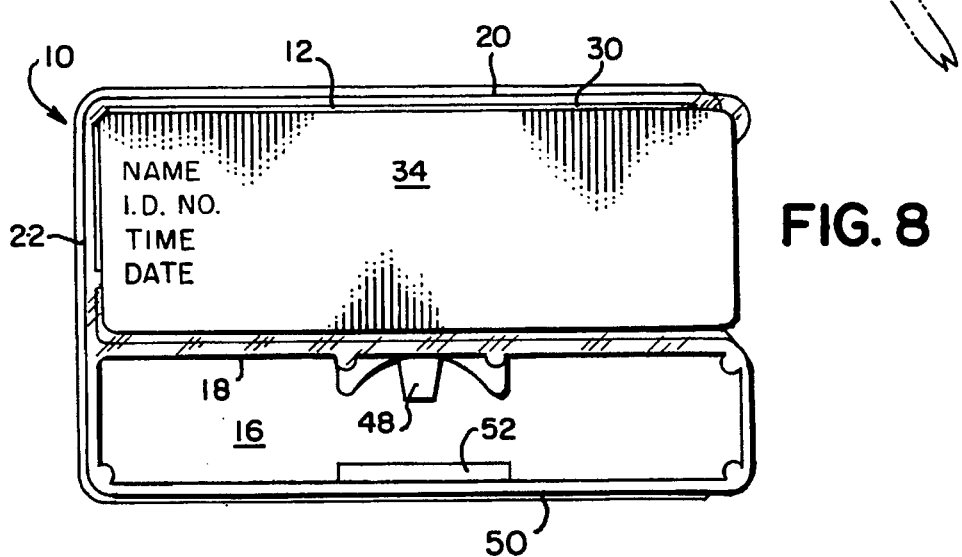
FIG. 8 shows the peelable label resealing the well in the test kit after insertion of the biopsy specimen.

FIG. 8 shows the use of the peelable sealing means 34 to re-seal the well 26 after insertion of the biopsy specimen. This peelable sealing means may also serve as a label to record the identity of the patient, the time and date of the test as shown in FIG. 8.

As shown in FIG. 1, the other side of the peelable sealing means 34 preferably carries a spectrum of colors and designations of the pH and negative (e.g. light green), slightly positive (e.g. medium green), moderately positive (e.g. dark green), and markedly positive responses (e.g. very dark green or blue), to this test. Other information and instructions may also be shown on this peelable label which can be read through the preferably transparent surface of the bottom wall 30 of compartment 14.

Other embodiments of the invention will be apparent from the preferred embodiments described above.

What is claimed is:

1. A test kit for diagnosing gastric disease by detecting a presence of *Helicobacter pylori* in a gastric biopsy specimen, which comprises:

an elongated body member divided into first and second parallel longitudinally extending upwardly open compartments;

the first compartment having a closed lower surface and walls upstanding from said first compartment lower surface at the rear, at one end, and between said first compartment and the second compartment; one end of said first compartment being open;

a well having an opening in said first compartment;

a peelable sealing means for opening and closing the opening of said well;

said well containing a composition containing urea and a dye indicator for detecting a presence of *Helicobacter pylori* in a gastric biopsy specimen inserted in the well;

said dye indicator comprising a combination of at least two dyes capable of providing to the biopsy specimen one of a spectrum of colors in response to presence of *Helicobacter pylori* in the biopsy specimen;

said peelable means having a color spectrum thereon for determining the presence of *Helicobacter pylori* by comparison with the color, as changed by the dye indicator, of the test biopsy specimen in the well; and said second compartment containing a pick for placing a gastric biopsy specimen in the well.

2. A test kit of claim 1 in which the lower surface of said first compartment has an indentation at the open end of said compartment and in which the peelable sealing means extends over said indentation to permit it to be grasped.

3. A test kit containing everything necessary for handling and testing a gastric biopsy specimen for a diagnosis of gastric disease, comprising, in combination:

a test composition containing urea and a dye indicator containing at least two dyes;

said test composition changing color in the presence of *H pylori* to a color distinctive from that of the biopsy specimen;

a color change occurring initially at an acid pH;

said kit also comprising means for containing and visibly displaying said test composition, and means for handling and placing a biopsy specimen in said test composition.

* * * * *

UNITED STATES PATENT AND TRADEMARK OFFICE
CERTIFICATE OF CORRECTION

PATENT NO. : 5,593,851
DATED : January 14, 1997
INVENTOR(S) : Frank W. Jackson

It is certified that error appears in the above-indentified patent and that said Letters Patent is hereby corrected as shown below:

Title page, item [54], and col. 1, should read-- TEST KIT FOR THE RAPID DETECTION OF HELICOBACTER PYLORI IN GASTRIC BIOPSY TISSUE--.

Signed and Sealed this

Eighth Day of April, 1997

Attest:

BRUCE LEHMAN

*Attesting Officer*          *Commissioner of Patents and Trademarks*